(12) United States Patent
Zinser et al.

(10) Patent No.: US 11,931,103 B2
(45) Date of Patent: Mar. 19, 2024

(54) METHOD AND DEVICE FOR CARRYING OUT THE METHOD IN A VEHICLE

(71) Applicant: Heidelberg Engineering GmbH, Heidelberg (DE)

(72) Inventors: Gerhard Zinser, Heidelberg (DE); Tilman Otto, Limburgerhof (DE)

(73) Assignee: Heidelberg Engineering GmbH, Heidelberg (DE)

( * ) Notice: Subject to any disclaimer, the term of this patent is extended or adjusted under 35 U.S.C. 154(b) by 984 days.

(21) Appl. No.: 16/475,357

(22) PCT Filed: Nov. 30, 2017

(86) PCT No.: PCT/EP2017/080974
§ 371 (c)(1),
(2) Date: Jul. 1, 2019

(87) PCT Pub. No.: WO2018/127330
PCT Pub. Date: Jul. 12, 2018

(65) Prior Publication Data
US 2021/0282636 A1    Sep. 16, 2021

(30) Foreign Application Priority Data
Jan. 5, 2017 (DE) .................... 10 2017 100 172.7

(51) Int. Cl.
*A61B 3/032* (2006.01)
*A61B 3/024* (2006.01)
(Continued)

(52) U.S. Cl.
CPC .............. *A61B 3/032* (2013.01); *A61B 3/024* (2013.01); *A61B 3/0325* (2013.01); *A61B 3/112* (2013.01);
(Continued)

(58) Field of Classification Search
CPC ....... A61B 3/113; A61B 3/032; A61B 3/0325; A61B 3/066; A61B 3/112; G02B 27/01
(Continued)

(56) References Cited

U.S. PATENT DOCUMENTS 5,422,690 A * 6/1995 Rothberg ............... A61B 3/113
351/221
6,097,295 A    8/2000 Griesinger
(Continued)

FOREIGN PATENT DOCUMENTS

DE    102004035896 A1    3/2006
DE    102012221647 A1 *  5/2014 ........... A61B 3/0083
(Continued)

OTHER PUBLICATIONS

Konstantopoulos P, Chapman P, Crundall D. Driver's visual attention as a function of driving experience and visibility. Using a driving simulator to explore drivers' eye movements in day, night and rain driving. Accid Anal Prev. May 2010;42(3):827-34. doi: 10.1016/j.aap.2009.09.022. PMID: 20380909. (Year: 2010).*
(Continued)

*Primary Examiner* — Zachary W Wilkes
(74) *Attorney, Agent, or Firm* — Katterle Nupp LLC; Paul Katterle; Robert Nupp (57) ABSTRACT

A method for examining a driver of a vehicle. In accordance with the method, at least one part of at least one eye and/or at least one part of the face of the driver is captured using a monitoring unit. The data captured by the monitoring unit is evaluated and the visual perception capability of the driver is examined based on the captured data. The method may further include identifying the driver and operating devices of the vehicle using the captured data.

13 Claims, 6 Drawing Sheets

(51) Int. Cl.
  *A61B 3/11* (2006.01)
  *A61B 3/113* (2006.01)
  *A61B 3/12* (2006.01)
  *A61B 5/00* (2006.01)
  *G02B 27/01* (2006.01)

(52) U.S. Cl.
  CPC .............. *A61B 3/113* (2013.01); *A61B 3/12* (2013.01); *A61B 5/6893* (2013.01); *G02B 27/01* (2013.01); *A61B 2503/22* (2013.01)

(58) Field of Classification Search
  USPC ................................................ 351/209, 211
  See application file for complete search history.

(56) References Cited

U.S. PATENT DOCUMENTS

| | | | |
|---|---|---|---|
| 6,386,706 | B1 | 5/2002 | McClure |
| 8,047,652 | B1* | 11/2011 | Collazo ............... A61B 3/0041 |
| | | | 351/239 |
| 8,184,867 | B2 | 5/2012 | Otto ..................... G06V 40/197 |
| | | | 382/117 |
| 9,480,393 | B2* | 11/2016 | Boate ....................... A61B 3/12 |
| 2010/0188639 | A1* | 7/2010 | Carda ..................... A61B 3/066 |
| | | | 351/242 |
| 2014/0333898 | A1* | 11/2014 | Boate .................. A61B 3/0008 |
| | | | 351/221 |
| 2015/0191152 | A1* | 7/2015 | Gennermann .......... B60R 25/04 |
| | | | 180/287 |

FOREIGN PATENT DOCUMENTS

| | | |
|---|---|---|
| DE | 102012221647 A1 | 5/2014 |
| DE | 102013003047 A1 | 8/2014 |
| EP | 0933743 A2 | 8/1999 |
| EP | 1997667 A1 | 12/2008 |
| EP | 2564766 A1 | 3/2013 |
| JP | S62109539 | 11/1985 |
| JP | 200595572 | 4/2005 |
| JP | 2008212359 | 9/2008 |
| JP | 2009169486 | 7/2009 |
| JP | 201638843 | 3/2016 |
| WO | WO9617545 A1 | 6/1996 |

OTHER PUBLICATIONS

Bronstad PM, et al.; Driving with Central Visual Field Loss II: How Scotomas above or below the Preferred Retinal Locus (PRL) Affect Hazard Detection in a Driving Simulator. PLoS One. Sep. 2, 2015;10(9):e0136517. doi: 10.1371/journal.pone.0136517. PMID: 26332315; PMCID: PMC4557943 (Year: 2015).*

Urwyler P, Gruber N, Müri RM, Jäger M, Bieri R, Nyffeler T, Mosimann UP, Nef T. Age-dependent visual exploration during simulated day- and night driving on a motorway: a cross-sectional study. BMC Geriatr. Feb. 28, 2015;15:18. doi: 10.1186/s12877-015-0015-2. PMID: 25888141; PMCID: PMC4350319. (Year: 2015).*

Mourant, R. R., & Rockwell, T. H. (1970). Mapping Eye-Movement Patterns to the Visual Scene in Driving: An Exploratory Study. Human Factors, 12(1), 81-87. https://doi.org/10.1177/001872087001200112 (Year: 1970).*

Kunimatsu-Sanuki S, Iwase A, Araie M, Aoki Y, Hara T, Nakazawa T, Yamaguchi T, Ono H, Sanuki T, Itoh M. An assessment of driving fitness in patients with visual impairment to understand the elevated risk of motor vehicle accidents. BMJ Open. Feb. 27, 2015 (Year: 2015).*

Crabb DP, Smith ND, Rauscher FG, Chisholm CM, Barbur JL, Edgar DF, Garway-Heath DF. Exploring eye movements in patients with glaucoma when viewing a driving scene. PLoS One. Mar. 16, 2010. (Year: 2010).*

Mackenzie AK, Harris JM. Eye movements and hazard perception in active and passive driving. Vis cogn. Jul. 3, 2015;23(6):736-757. doi: 10.1080/13506285.2015.1079583. Epub Sep. 7, 2015. PMID: 26681913; PMCID: PMC4673545. (Year: 2015).*

Seya Y, Nakayasu H, Yagi T. Useful field of view in simulated driving: Reaction times and eye movements of drivers. Iperception. Jun. 3, 2013;4(4):285-98. doi: 10.1068/10512. PMID: 24349688; PMCID: PMC3859571. (Year: 2013).*

Bronstad PM, Bowers AR, Albu A, Goldstein R, Peli E. Driving with central field loss I: effect of central scotomas on responses to hazards. JAMA Ophthalmol. Mar. 2013;131(3):303-9. doi: 10.1001/jamaophthalmol.2013.1443. PMID: 23329309; PMCID: PMC3605225. (Year: 2013).*

English translation of Internal Preliminary Report on Patentability and Written Opinion of the International Searching Authority for PCT/EP2017/080974.

International Search Report for PCT/EP2017/080974.

Written Opinion of the International Searching Authority for PCT/EP2017/080974.

* cited by examiner

METHOD AND DEVICE FOR CARRYING OUT THE METHOD IN A VEHICLE

CROSS-REFERENCE TO RELATED APPLICATION(S)

This application is the U.S. national phase of PCT Application No. PCT/EP2017/080974 filed on Nov. 30, 2017, which claims priority to German Patent Application No. 10 2017 100 172.7 filed on Jan. 5, 2017, the disclosures of which are incorporated in their entirety by reference herein.

TECHNICAL FIELD

The disclosure relates to a method for examining a driver of a vehicle and apparatus in the vehicle for carrying out the method.

BACKGROUND

Checking whether the eyes of a driver of a vehicle are open by means of an apparatus of the vehicle is known from DE 10 2004 035 896 A1.

DE 10 2013 003 047 A1 presents an apparatus of a vehicle by means of which a blinking pattern, more particularly double blinking, can be examined. By double blinking, a driver can select radio stations, for example.

EP 2 564 766 A1 discloses a method in which movements of a driver and objects in the driver's surroundings are sensed in order to infer the viewing direction of the driver.

DE 10 2012 221 647 A1 presents a method for testing the visual capability of a driver of a vehicle, in which method numbers of different size are displayed. The testing of color vision is also known.

The human eye can adapt its optical power to certain conditions. However, if this adaptability of the human eye is not sufficient for sharply imaging an image on the retina, the image is perceived blurrily. In particular, small details can no longer be optimally resolved.

The optical power of the eye is determined largely by the curvature of the outside of the cornea and the curvature of the adaptive lens. The geometric shape of these body parts is rarely optically optimal. The optical quality of these body parts progressively worsens from an optical central axis radially outward.

The imaging quality with a wide-open pupil, for example in twilight or at night, can be considerably impaired and thus can lead to an impairment in visual acuity (vision).

If optical imaging onto the retina is not optimal, the person instinctively squints. This reduces the effective size of the pupil and thus improves the sharpness of the optical imaging. The principle of the pinhole camera is used here, in particular when the pupil is wide open because of darkness.

However, limitations of or changes in the visual perception of a person can lead to hazardous situations if this person is driving a vehicle. Therefore, it is also necessary to recognize a driver who is suitable for driving and operating a vehicle.

The problem addressed by the disclosure is therefore that of monitoring, detecting and indicating limitations of and/or changes in the visual perception possibilities of a driver, identifying the driver and simplifying the operation of the vehicle.

SUMMARY

In accordance with the disclosure, a method for examining a driver of a vehicle is provided. In accordance with the method, at least one part of at least one eye and/or at least one part of the face of the driver is captured using a monitoring unit. The data captured by the monitoring unit is evaluated and the visual perception capability of the driver is examined based on the captured data.

BRIEF DESCRIPTION OF THE DRAWINGS

The features, aspects, and advantages of the present disclosure will become better understood with regard to the following description, appended claims, and accompanying drawings where:

DETAILED DESCRIPTION OF ILLUSTRATIVE EMBODIMENTS

According to the disclosure, it has been found that a monitoring unit must capture at least one part of at least one eye and/or at least one part of the face of the driver in order to obtain suitable information about movement characteristics or eye structures of the driver. It has then been found that the data captured by the monitoring unit must be evaluated in order to identify the driver and/or optionally to examine the driver's visual perception capability and/or the driver's eyes. Furthermore, it has been found that operation of devices of the vehicle or communication with these devices can be accomplished on the basis of the captured data.

After the driver has been identified, certain procedures or processes concerning the specific vehicle could be enabled. For example, highly secure biometric identification of the driver is conceivable.

Different areas of the human body are suitable for carrying out a biometric identification of a person. In general, fingerprints are used for this purpose, but the human iris and in particular the retina, with their unique structure, are highly suitable for identification.

Fingerprints are left behind everywhere in daily life and therefore disadvantageously disclose security-critical information. Furthermore, it is purely theoretically not possible for an imaging biometric monitoring unit, such as a camera, to distinguish the image of a biometric object from an image of a representation of the biometric object.

The retina is the only biometric structure that provides the possibility of communicating with the biometric monitoring unit during the detection of the retina structure. Information could be exchanged by showing patterns on the retina and by conscious eye movements. For example, a moving target or a PIN pad for entering a code could be used. This communication can occur between the eye and the biometric monitoring unit in such a way that the communication is secured against interception. This communication is extremely difficult to defeat. In this context, reference is made to U.S. Pat. No. 8,184,867 B2.

After the driver has been identified, the vehicle could be started. Secure identification could also make financial transactions and other transactions or contracts legally binding without the driver's signature. Therefore, entries of PINs and TANs or SMS authentications are no longer necessary. The initial storing of the eyes or eye structure of the driver in a data memory could be carried out at the authorized dealer of the vehicle by means of an identification card.

The viewing direction of the driver could be used to control devices of the vehicle or to communication with devices of the vehicle. If a monitoring unit of the vehicle is able to detect the viewing direction of the driver, then by looking at a region of a screen or of the head-up display and blinking once or twice the driver can activate certain functions or activate the displaying of additional information in these regions. This enables faster and more efficient operation of multimedia and navigation components, because optically monitored movements are sensed and used in addition to voice commands.

The monitoring unit could comprise a camera which, at standstill or during the trip of the vehicle, captures movements of the eyes and/or of a part of the face. The driver's eyes can be observed by means of a camera during the trip. It could thus be detected whether the driver squints over a relatively long period of time and/or looks at a traffic sign for an unusually long period of time. These captured data would be evaluated as indications that the driver apparently has difficulty reading the traffic sign. Particularly if there is an accumulation of such data captured by the monitoring unit, the monitoring unit or an apparatus of the vehicle could offer a visual acuity test within the vehicle.

In this context, the visual perception capability could be examined by displaying characters of different size, preferably numbers and/or letters, on a head-up display or a screen of the vehicle. An audio signal could be captured, each character to be recognized by the driver being marked and the marking moving to a further character when an audio signal corresponding to the character is captured. Specifically, the voice of the driver could be captured as an audio signal, each character to be recognized by the driver being marked and the marking moving to a further character if the driver has recognized the character to be recognized and has identified this character by means of their voice. It is thereby possible to test the visual capability of a driver quasi-incidentally, namely during the use of the vehicle. No other person besides the driver is necessary in order to carry out the vision test. A vision test image is preferably displayed by means of a head-up display installed in the vehicle.

The examination of the visual perception capability could be performed by displaying a first character, preferably numbers and/or letters, on a head-up display or a screen of the vehicle in a red-green contrast image. An audio signal could be captured and a further character and/or a further contrast image could be displayed if an audio signal corresponding to the first character is captured. Specifically, the voice of the driver could be captured as an audio signal and a further character and/or a further contrast image could be displayed if the driver has recognized the character to be recognized and has identified this character by means of their voice. It is thereby possible to test for color vision deficiency of a driver quasi-incidentally, namely during the use of the vehicle. No other person besides the driver is necessary in order to carry out the test for color vision deficiency.

Preferably, a contrast image is displayed by means of a head-up display installed in the vehicle. By means of individual contrast images having different levels of color contrast, the severity of a red-green color vision deficiency can also be determined.

The examination of the visual perception capability could be performed by examining the visual field and/or the central visual field of the driver. In this way, diseases of the eye can be detected.

The examination of the visual perception capability could be performed by displaying a grid having a dot at the center thereof on a head-up display or a screen of the vehicle. A test of the central visual field is thereby possible. A grid designed as a so-called Amsler grid enables a self-test for detecting central visual field defects, for example in case of age-related macular degeneration or other exudative or degenerative processes in the center of the retina.

The test preferably uses a large square grid having a dot at the center, which dot must be fixated during the examination. The other eye is usually completely covered by one's hand, which is held flat. In case of corresponding findings, the person to be examined will be able to notice apparent holes in the grid or dark spots in the pattern of the grid. Waves or distortions of the grid lines may also be perceived by the person. Such perceptions should always lead to an immediate ophthalmologic check.

The examination of the visual perception capability could be performed by examining the visual field of the driver. Glaucoma can thereby be detected. Particularly in case of so-called glaucoma, defects in the so-called visual field can occur. They are among the typical symptoms of this disease.

If glaucoma remains unnoticed or is not sufficiently medically treated, the afflicted person can even suffer a complete loss of vision and go blind. Globally, glaucoma is the second most frequent cause of blindness. In Germany, around one million people are afflicted, and the number of unreported cases is estimated to be on the same order of magnitude. By means of the method described here, it can be examined whether the driver is a person at risk during the trip.

In this context, viewing directions of the driver could be sensed over a defined time period during the trip. Thus, incidental measurement of visual field defects is enabled. The monitoring unit or an apparatus of the vehicle could sense the viewing direction of the driver. This could be accomplished by means of one or more cameras. In this process, the head orientation and the position of the pupils and/or of the iris relative to the head must be determined by means of an image-processing unit. In order to achieve highly precise measurement, a calibration procedure must be performed, possibly one time, for each driver.

The monitoring unit or the apparatus observes the viewing direction of the driver preferably continuously during the trip. As soon as an interesting object away from the current viewing direction of the driver is perceived, the driver will direct their fixation and/or viewing direction at this object in order to be able to more precisely resolve and observe this object. The resolution of the eye is namely considerably higher at the center of the visual field than further outside in the periphery.

By continuously observing the viewing behavior of the driver, a visual field map can be produced. Over hours, days, or weeks, a very dense map is thus produced, in which visual field defects (scotomas), i.e. locally restricted visual limitations or losses of vision, can be detected. It is also possible to create several visual field maps in dependence on the brightness of the stimulation, namely of the vehicle environment. In this way, even the extent of the limitation can be quantified. If a visual field defect is suspected, the monitoring unit or an apparatus of the vehicle recommends that an ophthalmologist be consulted.

The examination of the visual perception capability could be performed by displaying a changing pattern to the driver and by sensing changes in a pupil diameter of the driver by means of the monitoring unit. A central visual field measurement is thereby possible by means of pupillometry.

The driver could look for a few minutes at a changing pattern displayed on a head-up display or a screen of the vehicle. At the same time, the pupil diameter of both eyes could be measured by means of a camera. From the amount of the change in the pupil diameter over time in response to the pattern, which acts as a stimulation pattern, conclusions about the visual field can be made.

In order to be able to carry out this method, a sufficiently dark and homogeneous background is required. There could be such a background at night or during a night trip. The pupil diameter must be measured with high accuracy.

The examination of the visual perception capability could be performed by capturing a retinal image by means of the monitoring unit. Thus, a retinal image, namely a fundus image, can be produced. Many diseases of the retina can be seen in a fundus image, which could be captured by means of a laser scanning system with infrared illumination.

In this context, the monitoring unit could comprise a retinal scanner in the region of the sun visor or behind the sun visor. Thus, the sun visor can be used as a spacing or retaining means. By means of microelectromechanical scanning mirrors (MEMS), 2-D scanning systems can be constructed very compactly. However, in order to be able to capture a sufficiently large area of the ocular fundus, the head must be held relatively stable and an objective of the scanning head must be moved relatively close to the eye. The distance should be about 1-2 cm.

In order to hold the head, a sun visor folded down obliquely could be used as a forehead rest. For this purpose, a slight recess and/or enlargement could be provided in the sun visor for the positioning of the forehead. The driver could be moved up to the head support by means of a motorized seat. The scanning head could then be positioned in front of the two eyes in succession by electromechanical motorization and an image of the retina of each eye could be captured. Alternatively, two scanners or retinal scanners can be used to capture the images of the two eyes simultaneously.

The captured images could either be evaluated by the monitoring unit or an apparatus of the vehicle by means of an image analysis unit or be telemetrically transferred to a server and evaluated there either automatically or by an expert.

At the end of an examination, the visual perception capability of the driver could be qualified and/or a recommendation to consult a doctor could be presented. A driver can thereby be notified of health-related potential hazards to themselves and others immediately after or during a trip with the vehicle.

An apparatus of a vehicle for carrying out a method of the type described here could comprise a monitoring unit. The apparatus could also comprise a head-up display and/or further units. The apparatus can also be designed as an assembly of different interacting units.

Figure 1:
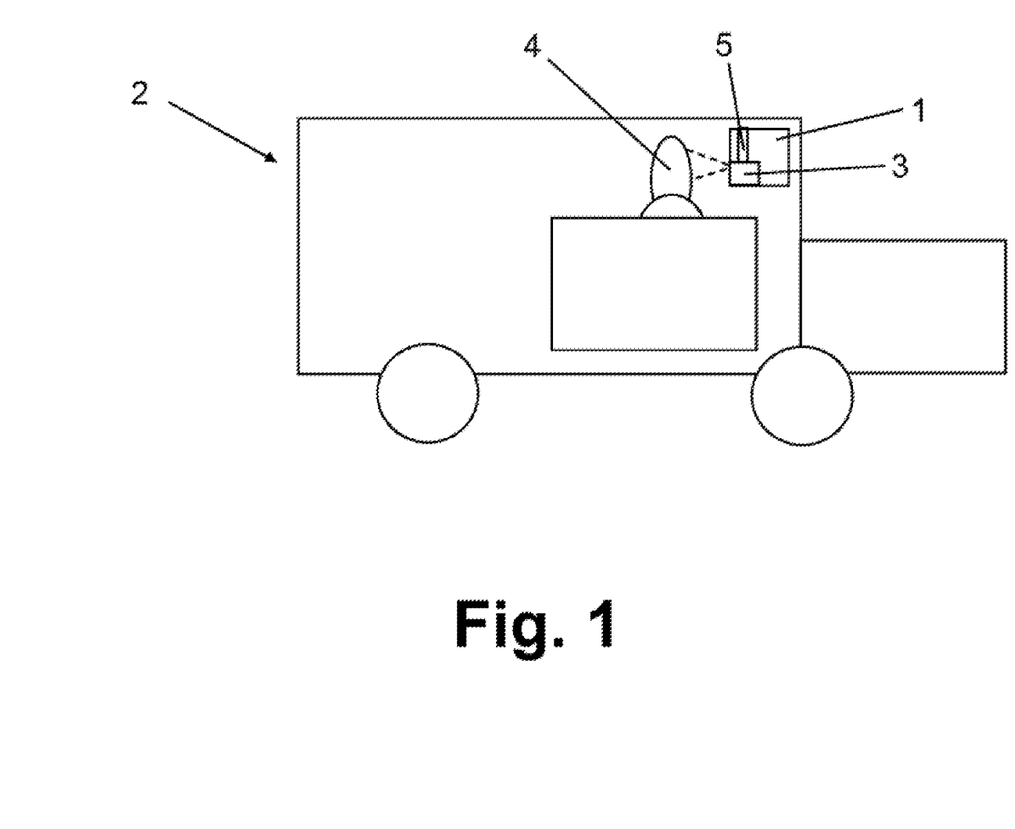
FIG. 1 is a schematic illustration of a motor vehicle, namely a passenger car or truck, which comprises an apparatus having a monitoring unit, by means of which the method described here can be carried out.

FIG. 1 shows an apparatus 1 of a vehicle 2, namely a motor vehicle, for carrying out a method of the type described below. The apparatus 1 comprises a monitoring unit 3 and a head-up display 5. The motor vehicle is a passenger car or a truck.

The method is used to recognize and/or indicate the driver 4 of the vehicle 2. The method is also used to detect and/or indicate limitations of the visual perception capability of the driver 4 of the vehicle 2. Finally, the method is used for the operation of the vehicle 2 by the driver 4. The method comprises the following steps:

capturing at least one part of at least one eye and/or at least one part of the face of the driver 4 by means of the monitoring unit 3, evaluating the data captured by the monitoring unit 3, identifying the driver 4 and/or examining the visual perception capability and/or the eyes of the driver 4 and/or operating devices of the vehicle 2 on the basis of the captured data.

The monitoring unit 3 comprises a camera, which, at standstill or during the trip of the vehicle 2, captures movements of the eyes and/or of a part of the face of the driver 4.

FIGS. 2 to 6 schematically show methods for detecting and/or indicating limitations of the visual perception capability of the driver 4 of the vehicle 2.

Such a method comprises the following steps: capturing at least one part of at least one eye and/or at least one part of the face of the driver 4 by means of the monitoring unit 3, evaluating the data captured by the monitoring unit 3, and examining the visual perception capability and/or the eyes of the driver 4 on the basis of the captured data.

Figure 2:
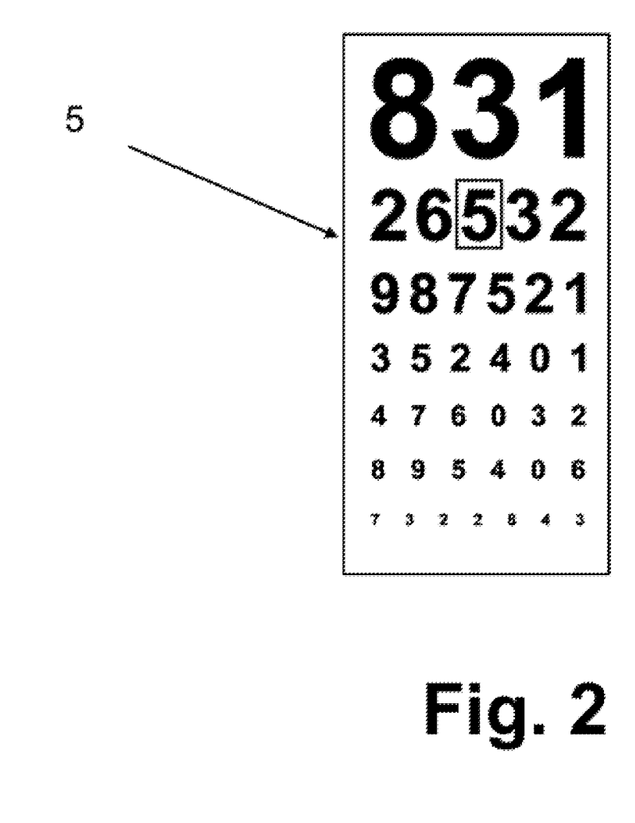
FIG. 2 is a visual presentation of numbers of different size, which are displayed by a head-up display in the motor vehicle in order to perform a test of visual acuity.

FIG. 2 shows that the examination of the visual perception capability is performed by displaying characters of different size, namely numbers, on a head-up display 5 of the vehicle 2.

An audio signal is captured. Each character to be recognized by the driver 4 is marked by a frame and the marking or the frame moves to a further character when an audio signal corresponding to the character is captured.

The voice of the driver 4 is captured as an audio signal. Each character to be recognized by the driver 4 is marked by the frame and the marking moves to a further character if the driver 4 has recognized the character to be recognized and has identified this character by means of their voice.

Figure 3:
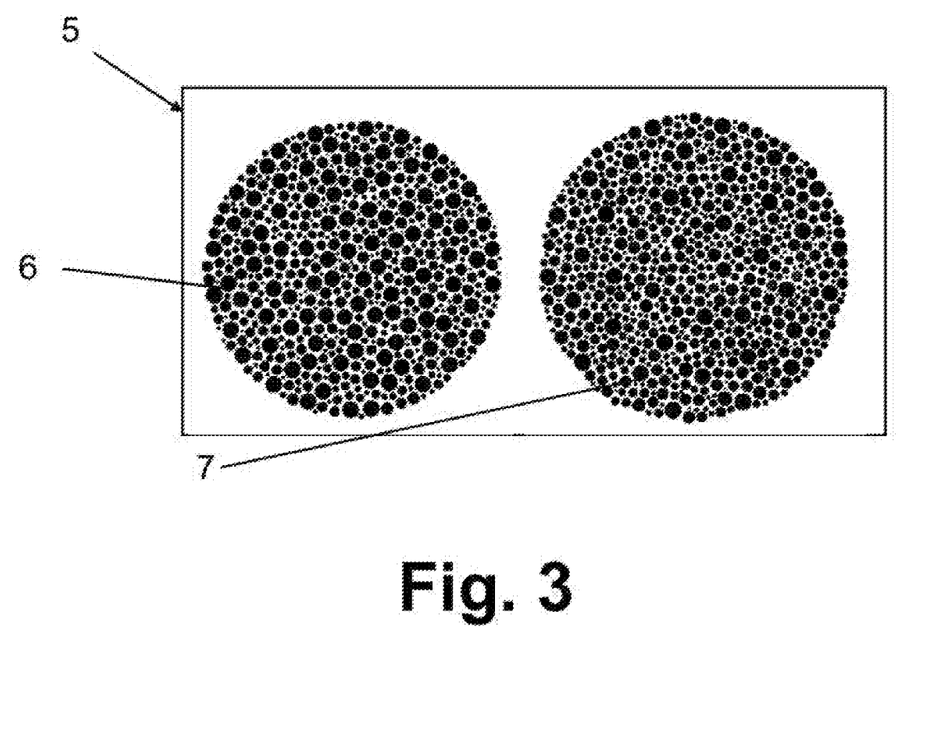
FIG. 3 is a presentation that enables a test for color vision deficiency to be performed, red-green color blindness being diagnosable by means of the left presentation and red-green color vision deficiency being diagnosable by means of the right presentation.

FIG. 3 shows that the examination of the visual perception capability is performed by displaying a number on a head-up display 5 of the vehicle 2 in a red-green contrast image 6.

An audio signal is captured, and a further number and a further contrast image 7 are displayed when an audio signal corresponding to the first number is captured.

The voice of the driver 4 is captured as an audio signal, and a further contrast image 7 is displayed if the driver 4 has recognized the number to be recognized in the first contrast image 6 and has identified this number by means of their voice.

Figure 4:
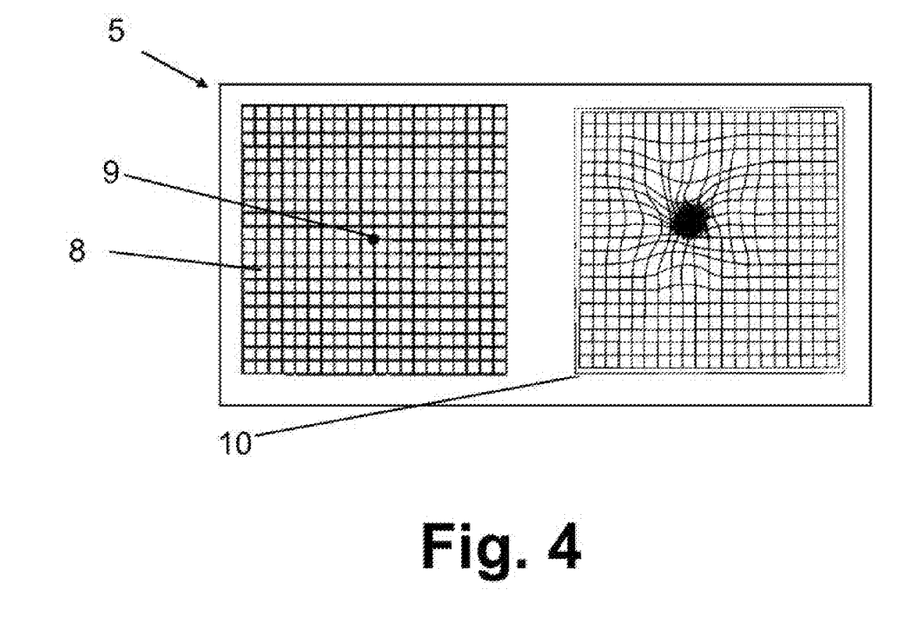
FIG. 4 is a presentation that enables an examination of the central visual field, a test pattern being shown on the left and an example of a pathological perception being shown on the right.

FIG. 4 shows that the examination of the visual perception capability is performed by displaying a grid 8 having a dot 9 at the center thereof on a head-up display 5 of the vehicle 2. A so-called Amsler grid is displayed.

The dot 9 at the center of the large square grid 8 is fixated with one eye during the test. The other eye is completely covered by one's hand, which is held flat.

In case of corresponding findings, the test subject will be able to notice apparent holes in the grid or dark spots in the grid pattern, and possibly waves or distortions of the grid lines. This is illustrated in the distorted grid 10.

Figure 5A:
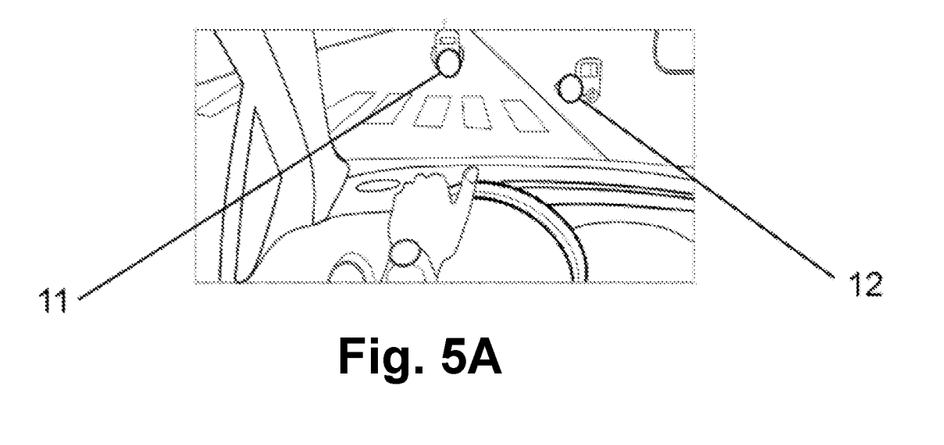
FIG. 5A is a schematic illustration of a visual field of a driver.
Figure 5B:
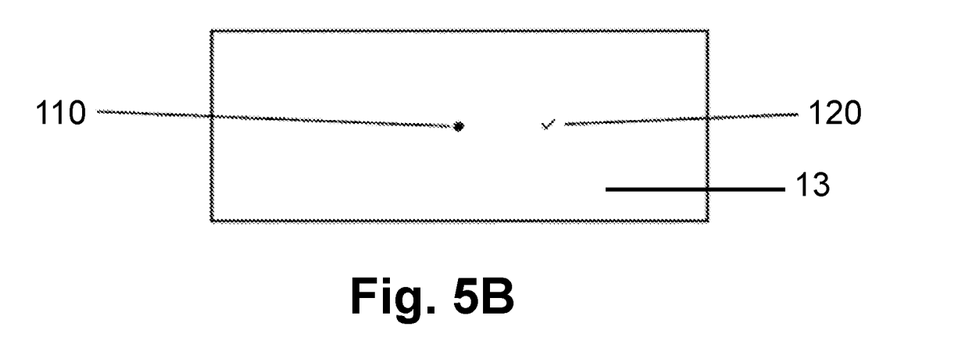
FIG. 5B is a map of the visual field that is starting to be populated and FIG. 5C is the visual field map after being densely populated.
Figure 5C:
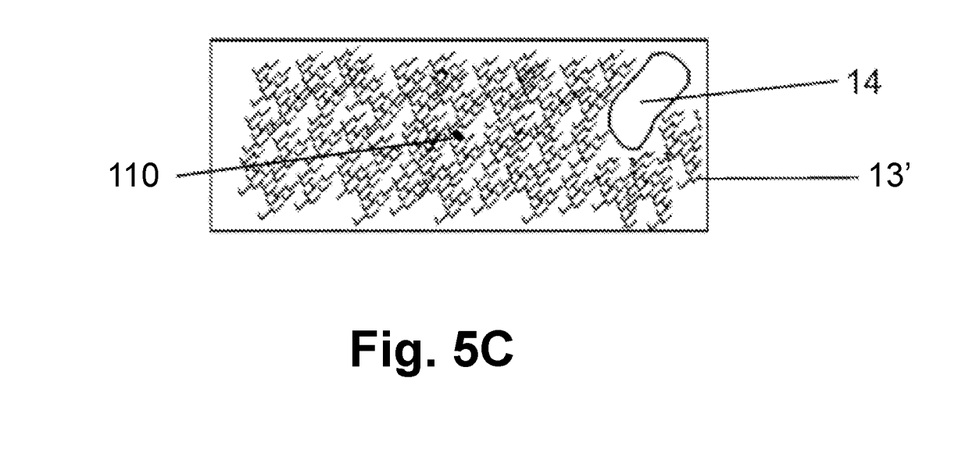

FIGS. 5A, 5B and 5C show that the examination of the visual perception capability is performed by examining the visual field of the driver 4.

Viewing directions of the driver 4 are sensed over a defined time period during the trip.

The apparatus 1 and/or the monitoring unit 3 senses the viewing direction of the driver 4. This can be accomplished by means of one or more cameras. In this process, the head orientation and the position of the pupils and/or of the iris relative to the head are determined by means of an image-processing unit. In order to achieve highly precise measurement, a calibration procedure is performed one time for the driver 4.

The monitoring unit 3 observes the viewing direction of the driver 4 continuously during the trip. If an interesting object away from the current viewing direction of the driver is perceived, the driver 4 will direct their fixation and/or viewing direction at this object in order to be able to more precisely resolve and observe this object. The resolution of the eye is considerably higher at the center of the visual field than further outside in the periphery.

In FIG. 5A, it is shown that a current viewing direction is directed at a first point 11, i.e. the visual field center is located there. If the viewing direction moves to the second point 12, the apparatus 1 or the monitoring device 3 registers that a stimulation to change view has occurred at this location in the peripheral visual field relative to the first point 11, i.e. the visual function is intact there.

The position of the second point 12 relative to the first point 11 is entered in a driver-specific visual field map 13, wherein in the visual field map 13, the first point 11 is represented by the point 110 and the second point 12 is represented by point 120. Over hours, days, or weeks, a very dense map 13' is thus produced, in which visual field defects 14 (scotomas), i.e. locally restricted visual limitations or losses of vision, can be detected.

It is also possible to create several maps in dependence on the brightness of the stimulation, namely of the vehicle environment. In this way, even the extent of the limitation can be quantified. If a visual field defect is suspected, the apparatus 1 of the vehicle 2 recommends that an ophthalmologist be consulted.

It is not graphically illustrated that the examination of the visual perception capability is performed by displaying a changing pattern to the driver 4 and by sensing changes in a pupil diameter of the driver 4 by means of the monitoring unit 3.

The driver 4 looks for a few minutes at a changing pattern displayed on the head-up display 5. At the same time, the pupil diameter of both eyes is measured by means of a camera. From the amount of the change in the pupil diameter over time in response to the pattern, which acts as a stimulation pattern, conclusions about the visual field can be made.

A sufficiently dark and homogeneous background is required for the function of this method. The pupil diameter is measured with high accuracy.

A method for the operation of a vehicle 2 by the driver 4 is not graphically illustrated. The method comprises the following steps: capturing at least one part of at least one eye and/or at least one part of the face of the driver 4 by means of the monitoring unit 3, evaluating the data captured by the monitoring unit 3, and operating devices of the vehicle 2 on the basis of the captured data.

It is not graphically illustrated that operation, namely in particular control of devices of the vehicle and/or communication with these devices, is accomplished by means of a viewing direction or on the basis of the viewing direction. The devices are controlled by the apparatus 1 after data, namely the viewing direction or blinking of the driver 4, have been captured.

The apparatus 1 and/or the monitoring unit 3 is able to detect the viewing direction of the driver 4. Thus, by looking at a screen region or head-up display region and/or blinking once or twice the driver 4 can activate certain functions or cause additional information to be displayed in these regions.

Figure 6A:
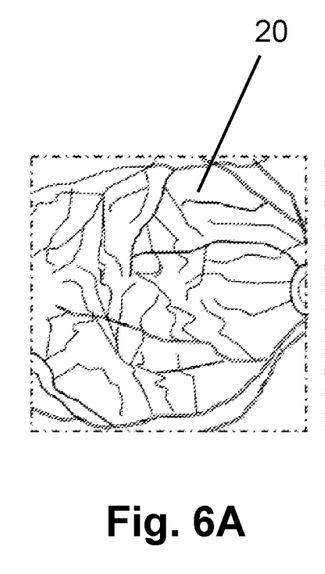
FIGS. 6A, 6B and 6C are retinal images, a normal fundus image being shown in FIG. 6A and pathological changes being shown in FIGS. 6B and 6C.
Figure 6B:
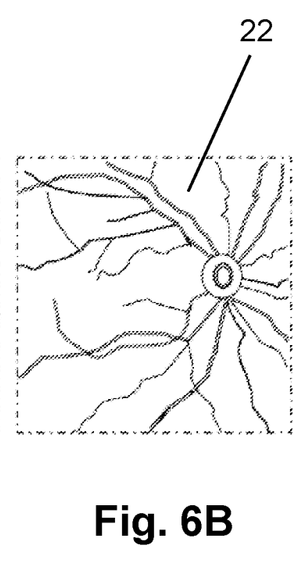
Figure 6C:
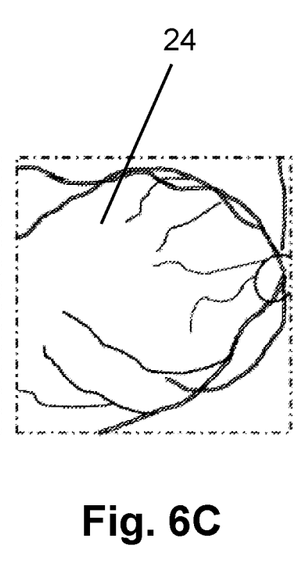

FIGS. 6A, 6B and 6C shows that the examination of the visual perception capability is performed by capturing retinal images by means of the monitoring unit 3. Specifically, three retinal images 20, 22, 24 are shown.

The monitoring unit 3 comprises a retinal scanner in the region of the sun visor or behind the sun visor.

Microelectromechanical scanning mirrors (MEMS) are used for this purpose. In order to be able to capture a sufficiently large area of the ocular fundus, the head is held stable and the objective of a scanning head is moved relatively close to the eye. A distance of about 1-2 cm is chosen.

In order to hold the head, a sun visor folded down obliquely is used as a forehead rest. A recess and an enlargement for the positioning of the forehead are provided in this sun visor.

The driver 4 is moved up to a head support by means of a motorized seat. The scanning head is then positioned in front of the two eyes in succession by electromechanical motorization and captures an image of the retina of each eye.

The captured images are either evaluated by the apparatus 1 itself by means of an image analysis unit or telemetrically transferred to a server and evaluated there either automatically or by an expert.

At the end of each examination described here, the visual perception capability of the driver 4 is qualified and/or a recommendation to consult a doctor is provided.

The qualification and/or recommendation can be presented as an audio signal, in the form of an electronic voice, or on a head-up display 5 or a screen.

A method for recognizing and/or indicating the driver 4 of a vehicle 2 is not graphically illustrated. The method comprises the following steps: capturing at least one part of at least one eye and/or at least one part of the face of the driver 4 by means of a monitoring unit 3, evaluating the data captured by the monitoring unit 3, and identifying the driver 4 on the basis of the captured data.

The method is used to recognize the driver 4 of the vehicle 2. A highly secure biometric identification of the driver is possible. The human iris and the retina, with their unique structure, are highly suitable for this purpose.

The retina is a biometric structure that provides the possibility of communicating with the apparatus 1 and/or the monitoring unit 3 during the detection of the retina structure. Information is exchanged by showing patterns on the retina, namely a moving target, and by conscious eye movements. This communication occurs between the eye and the apparatus 1 and/or the monitoring unit 3 in such a way that the communication is secured against interception. The identification of the driver 4 is used to start the vehicle 2.

The head-up display 5 is a display unit that enables the driver 4 to maintain their head posture or viewing direction when information is visually transmitted to the driver, because the information is projected into the driver's field of vision.

The invention claimed is:

1. A method for examining a driver of a motor vehicle having wheels and operable to move over roads, the method being performed in the motor vehicle and comprising:
   continuously monitoring with one or more cameras a viewing direction of the driver during a plurality of trips in the motor vehicle over a plurality of days,
   noting during each trip when the viewing direction of the driver changes from a center point to another point, wherein for each noted change in viewing direction of the driver, it is determined that a stimulation to change view has occurred at the other point in the peripheral visual field of the driver relative to the center point and that the driver's visual function is intact at the other point,
   forming a map populated with the noted center points and other points from the trips, and
   determining from the map whether the driver has a scotoma.

2. The method according to claim 1, wherein the one or more cameras during each trip of the motor vehicle, capture movements of the eyes and/or of a part of the face of the driver.

3. The method according to claim 1, further comprising:
   displaying characters of different size, comprising numbers and/or letters, on a head-up display or a screen of the motor vehicle;
   marking one of the displayed characters;
   capturing an audio signal; and
   if the captured audio signal corresponds to the marked character, marking another one of the displayed characters.

4. The method according to claim 1, further comprising:
   displaying a first character, comprising a number or a letter, on a head-up display or a screen of the motor vehicle in a red-green contrast image;
   capturing an audio signal; and
   if the captured audio signal corresponds to the displayed first character, displaying a second character comprising a number or a letter.

5. The method according to claim 1, wherein a scotoma is detected from a blank area in the map.

6. The method according to claim 1, further comprising:
   displaying a grid having a dot at the center thereof on a head-up display or a screen of the motor vehicle.

7. The method according to claim 1, further comprising:
   displaying a changing pattern to the driver and sensing changes in a pupil diameter of the driver using the one or more cameras.

8. The method according to claim 1, further comprising:
   capturing a retinal image using a monitoring unit.

9. The method according to claim 8, wherein the monitoring unit comprises one or two retinal scanners in the region of a sun visor of the motor vehicle or behind the sun visor.

10. The method according to claim 9, further comprising identifying the driver from the retinal image.

11. The method according to claim 10, further comprising using the identification of the driver to start the motor vehicle.

12. The method according to claim 1, further comprising: recommending that the driver consult a doctor if a scotoma is detected.

13. The method of claim 1, wherein the trips are original trips, and wherein the method further comprises:
   continuously monitoring with the one or more cameras a viewing direction of the driver during a plurality of other trips over a plurality of days, wherein the brightness inside the motor vehicle during the other trips is different than the brightness inside the motor vehicle during the original trips;
   noting during each other trip when the viewing direction of the driver changes from a center point to another point,
   forming a second map populated with the noted center points and other points from the other trips;
   using the first and second maps to determine whether the driver has a scotoma and, if so, quantifying the extent of the scotoma.

* * * * *